(12) United States Patent
Nam et al.

(10) Patent No.: US 11,986,271 B2
(45) Date of Patent: May 21, 2024

(54) APPARATUS AND METHOD FOR MEASURING BIO-SIGNAL

(71) Applicants: SAMSUNG ELECTRONICS CO., LTD., Suwon-si (KR); POSTECH Research and Business Development Foundation, Pohang-si (KR)

(72) Inventors: Sung Hyun Nam, Yongin-si (KR); Chulhong Kim, Pohang-si (KR); Ka Ram Choi, Yongin-si (KR); Jin Young Kim, Pohang-si (KR); Jin Woo Baik, Pohang-si (KR); Joongho Ahn, Pohang-si (KR)

(73) Assignees: SAMSUNG ELECTRONICS CO., LTD., Suwon-si (KR); POSTECH Research and Business Development Foundation, Pohang-si (KR)

( * ) Notice: Subject to any disclaimer, the term of this patent is extended or adjusted under 35 U.S.C. 154(b) by 116 days.

(21) Appl. No.: 17/677,059

(22) Filed: Feb. 22, 2022

(65) Prior Publication Data

US 2023/0157551 A1 May 25, 2023

(30) Foreign Application Priority Data

Nov. 24, 2021 (KR) ........................ 10-2021-0163083

(51) Int. Cl.
*A61B 5/00* (2006.01)
*A61B 5/024* (2006.01)

(52) U.S. Cl.
CPC ........ *A61B 5/0095* (2013.01); *A61B 5/02416* (2013.01)

(58) Field of Classification Search
CPC . A61B 5/0075; A61B 5/02416; A61B 5/0062; A61B 5/02007; A61B 5/14532;
(Continued)

(56) References Cited

U.S. PATENT DOCUMENTS 9,535,159 B2 * 1/2017 Ebisawa ............ G01N 29/2418
9,737,216 B2 * 8/2017 Nanaumi ............ A61B 5/0075
(Continued)

FOREIGN PATENT DOCUMENTS

CN 107427219 A 12/2017
JP 2012187394 A 10/2012
(Continued)

OTHER PUBLICATIONS

Baik, J., et al., "Super Wide-Field Photoacoustic Microscopy of Animals and Humans In Vivo", IEEE Transactions on Medical Imaging, vol. 39, Apr. 2020, pp. 1-3 (Abstract only).
(Continued)

*Primary Examiner* — Christopher L Cook
*Assistant Examiner* — Dean N Edun
(74) *Attorney, Agent, or Firm* — Sughrue Mion, PLLC

(57) ABSTRACT

An apparatus for measuring a bio-signal includes: a light source configured to emit light; an ultrasonic transducer configured to obtain a photoacoustic signal generated from an object; a photoacoustic coupler disposed in contact with the ultrasonic transducer and configured to direct the light transmitted from the light source to a scanner and to direct the photoacoustic signal generated from the object to the ultrasonic transducer; the scanner configured to reflect the light incident from the photoacoustic coupler to the object, and reflect the photoacoustic signal generated from the object to the photoacoustic coupler; a scanner controller configured to adjust a light incident position on the object by controlling the angle of the scanner; a light detector configured to obtain a light signal by detecting the light scattered or reflected from the object; and a processor configured to obtain bio-information based on the light signal and the photoacoustic signal.

16 Claims, 8 Drawing Sheets

(58) Field of Classification Search
CPC ... A61B 5/0095; A61B 5/1455; A61B 5/0064; A61B 5/0033; A61B 5/0035; A61B 5/0097
See application file for complete search history.

(56) References Cited

U.S. PATENT DOCUMENTS

| | | | |
|---|---|---|---|
| 10,624,543 B2 | 4/2020 | Zheng et al. | |
| 2010/0268042 A1* | 10/2010 | Wang | A61B 5/14546 73/587 |
| 2011/0263955 A1* | 10/2011 | Narita | A61B 1/00096 356/342 |
| 2013/0109941 A1* | 5/2013 | Li | G01N 21/49 600/407 |
| 2014/0268163 A1* | 9/2014 | Milner | A61B 6/03 356/451 |
| 2017/0014031 A1* | 1/2017 | Lim | A61B 5/0095 |
| 2017/0303829 A1* | 10/2017 | Cohen | A61B 5/0075 |
| 2020/0214603 A1* | 7/2020 | Ghiasi | A61B 5/4842 |
| 2021/0052164 A1* | 2/2021 | Shnaiderman | A61B 5/14546 |

FOREIGN PATENT DOCUMENTS

| | | |
|---|---|---|
| JP | 6366367 B2 | 8/2018 |
| JP | 2021515638 A | 6/2021 |

OTHER PUBLICATIONS

Tamura, T., et al., Wearable Photoplethysmographic Sensors—Past and Present, Electronics, vol. 3, Apr. 23, 2014, pp. 282-302.

* cited by examiner

APPARATUS AND METHOD FOR MEASURING BIO-SIGNAL

CROSS-REFERENCE TO RELATED APPLICATION(S)

This application claims priority from Korean Patent Application No. 10-2021-0163083, filed on Nov. 24, 2021, in the Korean Intellectual Property Office, the disclosure of which is incorporated herein by reference in its entirety.

BACKGROUND

1. Field

Apparatuses and methods consistent with example embodiments relate to measuring a bio-signal in a non-invasive manner.

2. Description of Related Art

Photoacoustic microscopy is a next-generation medical imaging technology that fuses the principles of optical imaging and ultrasound imaging, and has recently been spotlighted in various preclinical and clinical research fields. A photoacoustic microscopy system irradiates a portion of a target to be inspected with a laser beam and subsequently measures ultrasound generated according to the amount of laser beam absorbed to the target to thus acquire a three-dimensional (3D) image of the intended portion of the target. Unlike a CT or X-ray system, the photoacoustic microscope system does not use ionizing radiation, and can be implemented in a shorter period of time and at lower cost compared to magnetic resonance imaging (MRI) or positron emission tomography (PET). In addition, the photoacoustic microscopy system can acquire an image of a deeper section compared to an optical image, and can provide functional information, such as blood oxygen saturation or the like, that cannot be obtained from an ultrasound image. The photoacoustic microscopy system may serve as an imaging platform for preclinical small animal research and clinical research by acquiring various pathological information based on the light absorption properties of living tissues that can be obtained from photoacoustic microscopy.

With the aging population, increased medical costs, and a lack of medical personnel for specialized medical services, research is being actively conducted on information technology (IT)-medical convergence technologies, in which IT technology and medical technology are combined. Particularly, monitoring of a health condition of a human body may not be limited to places such as hospitals, but is expanded by mobile healthcare fields that may monitor a user's health condition anywhere (e.g., at home or office on in transit from one place to another place) and anytime in daily life. Some examples of bio-signals, which indicate the health condition of individuals, may include an electrocardiography (ECG) signal, a photoplethysmography (PPG) signal, an electromyography (EMG) signal, and the like, and various bio-signal sensors are being developed to measure the bio-signals in daily life.

SUMMARY

According to an aspect of an example embodiment, there is provided an apparatus for measuring a bio-signal, the apparatus including: a light source configured to emit light; an ultrasonic transducer configured to obtain a photoacoustic signal generated from an object; a photoacoustic coupler disposed in contact with the ultrasonic transducer and configured to direct the light transmitted from the light source to a scanner and to direct the photoacoustic signal generated from the object to the ultrasonic transducer; the scanner configured to reflect the light incident from the photoacoustic coupler to the object, and reflect the photoacoustic signal generated from the object to the photoacoustic coupler; a scanner controller configured to adjust a light incident position on the object by controlling an angle of the scanner; a light detector configured to obtain a light signal by detecting the light scattered or reflected from the object; and a processor configured to obtain bio-information based on the light signal and the photoacoustic signal, wherein the processor is configured to obtain a blood vessel image of the object based on the photoacoustic signal for each light incident position.

The apparatus may further include a scanner controller configured to adjust a light incident position on the object by controlling a tilt angle of the scanner.

The processor may be configured to obtain a blood vessel image of the object based on the photoacoustic signal for each light incident position, and obtain a photoplethysmography (PPG) signal according to a distance between the adjusted light incident position and the light detector.

The apparatus may further include a plurality of light detectors comprising the light detector, wherein the processor may be further configured to compute an average or a weight sum of an amount of light detected by each of the plurality of light detectors.

The processor may be further configured to assign a weight based on a distance between a light incident position on the object and each of each of the plurality of detectors.

The apparatus may further include a light transmitter configured to transmit the light emitted from the light source to the photoacoustic coupler.

The light transmitter may include an objective lens for condensing the light emitted from the light source to the photoacoustic coupler.

The processor may be configured to pulse drive the light source, or to continuously drive the light source by modulating a light intensity according to time.

According to an aspect of another example embodiment, there is provided an apparatus for measuring a bio-signal, the apparatus including: a first light source configured to emit a first light; an ultrasonic transducer configured to obtain a photoacoustic signal generated from an object; a photoacoustic coupler disposed in contact with the ultrasonic transducer and configured to reflect the first light transmitted from the first light source to a scanner and to direct the photoacoustic signal generated from the object to the ultrasonic transducer; the scanner configured to reflect the light incident from the photoacoustic coupler to the object, and reflect the photoacoustic signal generated from the object to the photoacoustic coupler; a second light source configured to emit a second light to measure a photoplethysmography (PPG) signal; a light detector configured to measure a light signal by detecting the second light scattered or reflected from the object; and a processor configured to obtain bio-information based on the light signal and the photoacoustic signal.

The apparatus may further include a scanner controller configured to adjust a light incident position on the object by controlling a tilt angle of the scanner.

The apparatus may further include a light transmitter configured to transmit the first light and the second light to the photoacoustic coupler.

The light transmitter may include an objective lens for condensing the first light and the second light to the photoacoustic coupler.

The processor may be further configured to obtain a blood vessel image of the object based on the photoacoustic signal for each light incident position, and to obtain a PPG signal according to a distance between the light incident position and the light detector.

The first light may be reflected by the photoacoustic coupler and the scanner to be incident to the object and the second light source may be configured to emit the second light directly to the object.

The apparatus may include a plurality of light detectors comprising the light detector, wherein the processor may be configured to compute an average or a weighted sum an amount of light detected by each of the plurality of light detectors.

The processor may be further configured to assign a weight based on a distance between a light incident position on the object and each of the plurality of light detectors.

The processor may be further configured to control the second light source to emit the second light of a plurality of wavelength ranges, and to assign a wavelength-specific weight to an amount of light of each wavelength detected by the light detector.

At least one of a wavelength and an intensity of the first light and the second light are different from each other.

The processor may be further configured to drive the first light source when the scanner rotates in a first direction, and to drive the second light source when the scanner rotates in a second direction.

According to an aspect of another example embodiment, there is provided a method of measuring a bio-signal, the method including: emitting light; directing the light to a scanner, by a photoacoustic coupler disposed in contact with an ultrasonic transducer; directing the light incident from the photoacoustic coupler to an object, by the scanner having an adjustable tilt angle; obtaining, by the ultrasonic transducer, a photoacoustic signal generated from the object and then is received through the scanner and the photoacoustic coupler; and measuring, at a light detector, a light signal by detecting the light scattered or reflected from the object.

BRIEF DESCRIPTION OF THE DRAWINGS

The above and/or other aspects will be more apparent by describing certain example embodiments, with reference to the accompanying drawings, in which.

DETAILED DESCRIPTION

Figure 1:
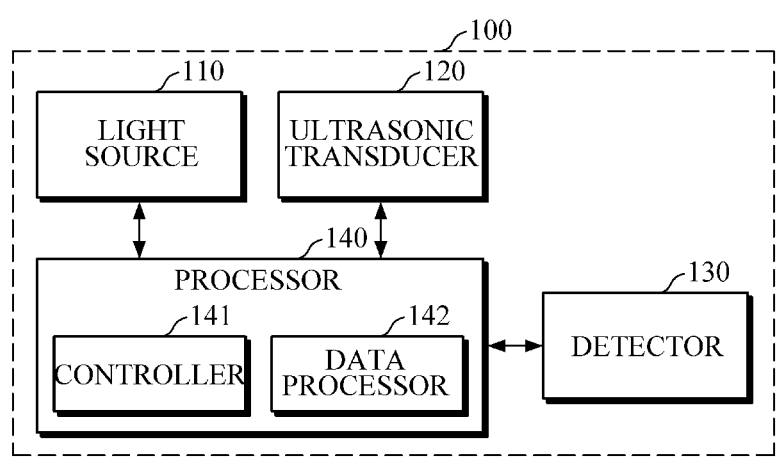
FIG. 1 is a block diagram illustrating an apparatus for measuring a bio-signal according to an exemplary embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software. Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

FIG. 1 is a block diagram illustrating an apparatus for measuring a bio-signal according to an exemplary embodiment.

Referring to FIG. 1, an apparatus 100 for measuring a bio-signal according to an exemplary embodiment may include a light source 110, an ultrasonic transducer 120, a detector (e.g., a light detector) 130, and a processor 140.

The light source 110 may emit light. In this case, the light source 110 may include a light emitting diode (LED), a laser diode (LD), and a phosphor, but is not limited thereto. The wavelength range of light emitted by the light source 110 may include various wavelength ranges, such as the infrared (IR) range, the visible light range, the near infrared (NIR) range, etc.

The ultrasonic transducer 120 may measure or obtain a photoacoustic signal based on light reflected or incident from an object. That is, the ultrasonic transducer 120 may measure a photoacoustic signal that is an ultrasonic signal generated due to the thermal expansion of the object that has absorbed light. The ultrasonic transducer 120 may include a plurality of ultrasonic elements arranged in a linear one-dimensional or two-dimensional array. In this case, the ultrasonic elements may be formed of piezoelectric elements.

The object may be a body part of a user, for example, a region of a wrist surface adjacent to the radial artery, or a human skin area where the capillary blood or venous blood passes through. However, the object is not limited thereto, and may be a distal body portion, such as a finger, a toe, or the like, which has a high density of blood vessels.

The detector 130 may measure a light signal by detecting light scattered or reflected from the object. In this case, the light signal may be a photoplethysmography (PPG) signal used for measuring blood sugar, blood pressure, or the like of the user, but is not limited thereto. Hereinafter, for convenience of description, a PPG signal will be taken as an example of the bio-signal.

The detector 130 may include a photodiode, a phototransistor, and the like. However, the detector 130 is not limited thereto, and may include a complementary metal-oxide semiconductor (CMOS) image sensor, a charge-coupled device (CCD) image sensor, and the like. Here, the detector 130 may be provided in plural.

When the light emitted from the light source 110 reaches the object, some part of the light is absorbed inside the living tissues and converted into photoacoustic signals and returns back in the form of ultrasound, and some other part of the light is reflected and returns back in the form of light. At this time, the returning ultrasound is measured by the ultrasonic transducer 120, and the reflected light is detected by the detector 130. In this case, there may be only a very short time delay between the photoacoustic signal detection by the ultrasonic transducer 120 and the PPG signal measurement by the detector 130, so that the two signals are naturally synchronized with each other. By measuring the synchronized photoacoustic signal and PPG signal, it is possible to identify changes associated with hemodynamics of the living body with a high spatial and temporal resolution.

The processor 140 may be electrically connected to the light source 110, the ultrasonic transducer 120, the detector 130, and the like, and may include a controller 141 and a data processor 142.

Figure 2A:
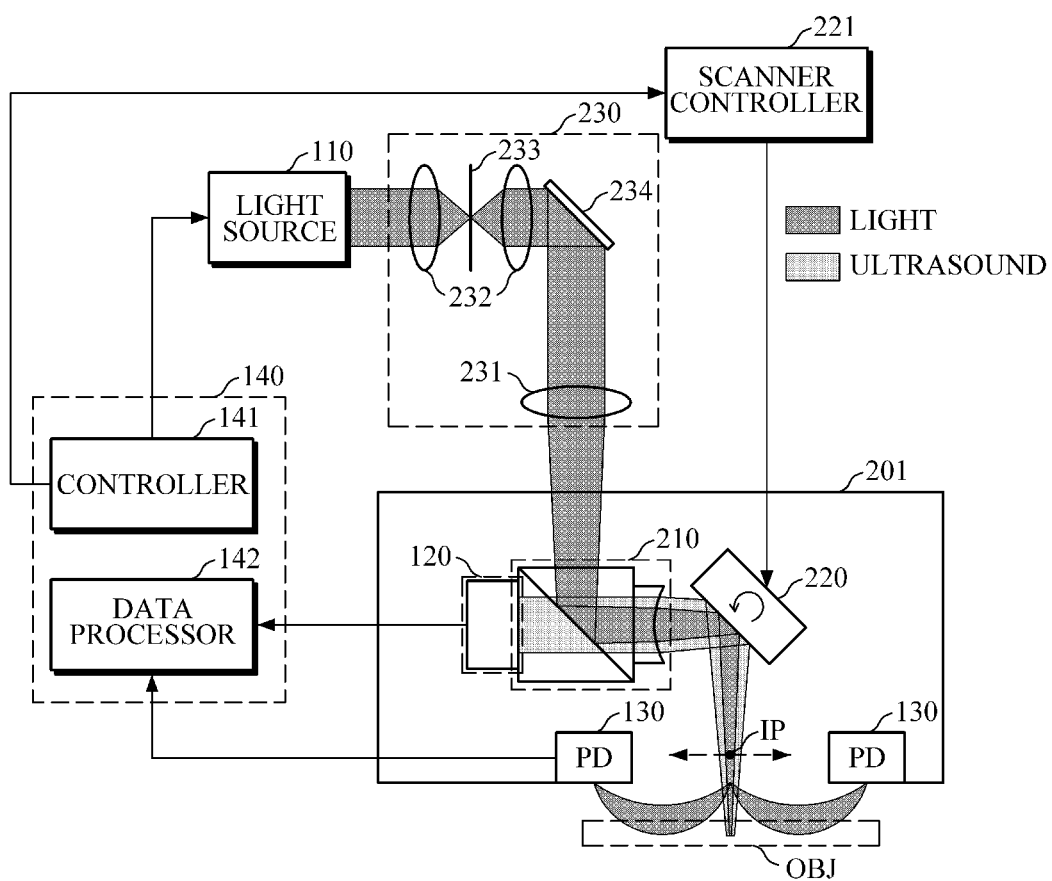
FIG. 2A is a diagram illustrating the apparatus for measuring a bio-signal of FIG. 1 according to an exemplary embodiment.

The controller 141 may control the operation of at least one of the light source 110, the ultrasonic transducer 120, the detector 130, a scanner (e.g., a scanner 220 in FIG. 2A), and a scanner controller (e.g., a scanner controller 221 in FIG. 2A).

For example, the controller 141 may control the intensity, wavelength, and the like of the light to be emitted by the light source 110. For example, the controller 141 may control the light source 110 to emit light in a pulse driving manner, or to continuously emit light (in a constant wave manner), while controlling the light source 110 to modulate the light intensity according to time.

Alternatively, the controller 141 may generate a synchronization signal for emitting light from the light source 110, and in this case, the light source 110 may emit light according to the synchronization signal generated by the controller 141.

In another example, the controller 141 may control a tilt angle of the scanner through the scanner controller to adjust the light incident position on the object.

A structure of the apparatus for measuring a bio-signal, including the light source 110, the ultrasonic transducer 120, the detector 130, and the scanner, will be described with reference FIG. 2A. FIG. 2A is a diagram illustrating the apparatus for measuring a bio-signal of FIG. 1 according to an exemplary embodiment.

Referring to FIG. 2A, the apparatus for measuring a bio-signal includes a housing 201, a photoacoustic coupler 210, a scanner 220, a scanner controller 231, and a light transmitter 230 in addition to the light source 110, the ultrasonic transducer 120, and the detector 130 that are described above.

FIG. 2A illustrates that there are two detectors 130, but the number of detectors 130 is not limited thereto.

The housing 201 may contain a conductive fluid, such as water, or a non-conductive fluid, to increase the efficiency of photoacoustic signal measurement. As illustrated in FIG. 2A, the photoacoustic coupler 210, the scanner 220, and the detectors 130 may be disposed in the housing 201.

The photoacoustic coupler 210 may be disposed in contact with the ultrasonic transducer 120, but is not limited thereto.

The photoacoustic coupler 210 may reflect the light that is emitted from the light source 110 and transmitted by the light transmitter 230 in a direction of the scanner 220. In addition, the photoacoustic coupler 210 may allow a photoacoustic signal generated from an object to pass therethrough in a direction of the ultrasonic transducer 120. Also, light and ultrasound may be coupled into one path and focal points of the light and ultrasound may be aligned to the same height. In this case, the photoacoustic coupler 210 may be made of aluminum or gold material to reflect the light and pass the photoacoustic signal, but is not limited thereto.

The photoacoustic coupler 210 may be omitted, and in this case, the ultrasonic transducer 120 may be a ring transducer that has an empty space at the center thereof to couple light and ultrasound into one path, but is not limited thereto. The ring transducer may include a focused ring transducer and a non-focused ring transducer. The non-focused ring transducer may include an acoustic lens.

The scanner 220 may be disposed between the photoacoustic coupler or the ultrasonic transducer and the object on the light path, but is not limited thereto. In this case, as illustrated in FIG. 2A, the ultrasonic transducer 120, the photoacoustic coupler 210, and the scanner 220 may be horizontally disposed in a row, but various exemplary embodiments of the present disclosure are not limited thereto.

The scanner 220 may reflect the light reflected by the photoacoustic coupler 210 in the direction of the object, and may reflect the ultrasound generated from the object in the direction of the photoacoustic coupler 210.

The scanner 220 may include a typical motor-based device, an actuator, or a galvanometer scanner, but is not limited thereto. Any type of scanner may be used without limitation depending on the type of fluid (e.g., conductive fluid, such as water, or non-conductive fluid) contained in the apparatus 100 for measuring a bio-signal. A mirror surface of the scanner 220 may be coated with aluminum or gold to simultaneously reflect light and ultrasound in the fluid, but is not limited thereto.

The scanner 220 may be configured such that the angle thereof can be adjusted, and the scanner controller 221 may control the angle of the scanner 220. The scanner controller 221 may include a motor-based device or an actuator, but is not limited thereto.

For example, the scanner controller 221 may control the scanner 220 to vibrate and rotate in a reciprocal manner within a predetermined angle range (e.g., within 20 degrees). In this case, the scanner controller 221 may adjust a light incident position IP on the object OBJ by controlling the angle of the scanner 220.

In addition, as the apparatus 100 for measuring a bio-signal includes the scanner 220, light and ultrasound can be scanned fast, thereby improving a scanning speed.

The light transmitter 230 may transmit the light emitted from the light source 110 in the direction of the photoacoustic coupler 210 and/or the ultrasonic transducer 120.

The light transmitter 230 may include collimators 232 that make the light emitted from the light source 110 into a parallel light beam, a pin hole 233 disposed between the collimators 232, a light reflective mirror 234, and an objective lens 231 that condenses the parallel light beam to the photoacoustic coupler 210. FIG. 2A illustrates that there are two collimators 232, but various exemplary embodiments of the present disclosure are not limited thereto. Some parts of the light transmitter 230 may be omitted. The light transmitter 230 may further include other parts for transmit the light emitted from the light source 110 in the direction of the ultrasonic transducer 120 and/or the photoacoustic coupler 210.

Referring back to FIG. 1, the data processor 142 may receive the photoacoustic signal measured by the ultrasonic transducer 120 and the PPG signal measured by the detector 130 and synchronized with the photoacoustic signal.

The data processor 142 may acquire a blood vessel image of the subject based on the received photoacoustic signal.

In particular, the data processor 142 may amplify the received photoacoustic signal. At this time, the data processor 142 may include a pulse generator-receiver or a radio frequency (RF) amplifier, but is not limited thereto.

The data processor 142 may obtain the blood vessel image based on the received photoacoustic signal or the result of amplifying the photoacoustic signal. For example, the data processor 142 may obtain the blood vessel image of the object by performing image-processing on the photoacoustic signals for each light incident position that is changed as the angle of the scanner is controller.

The data processor 142 may preprocess the received PPG signal.

For example, the data processor 142 may perform preprocessing, such as filtering for removing noise from the received PPG signal, signal amplification, conversion into a digital signal, or the like. In this case, the data processor 142 may perform bandpass filtering of 0.4 Hz to 10 Hz using a bandpass filter to remove noise from the light detection result. Also, the data processor 142 may perform correction through fast Fourier transform-based reconstruction of the PPG signal. Alternatively, the data processor 142 may remove noise by using a common mode filter. However, various exemplary embodiments of the present disclosure are not limited thereto, and various types of preprocessing may be performed according to various measurement environments, such as computing performance or measurement accuracy of the apparatus, the purpose of bio-signal measurement, the measurement part of the user, the temperature of the object, humidity, and the like. A separate analog circuit or digital circuit may be used for the preprocessing.

When the detector 130 is provided in plural, the data processor 142 may combine the amounts of light detected by each of the detectors 130. For example, the data processor 142 may average the amounts of light detected by each of the detectors 130, or assign a weight to each of the detected amounts of light according to predetermined criteria, to obtain a weighted sum of the amounts of light.

In this case, the data processor 142 may assign a weight based on a distance between the adjusted light incident position on the object and each of the detectors 130.

For example, in FIG. 2A, when the scanner 220 rotates in a clockwise direction, the light incident position is moved to the left and becomes closer to the left detector of the two detectors, and thus the amount of light detected by the left detector will increase. Meanwhile, the light incident position becomes farther from the right detector, and thus the amount of light detected by the right detector will decrease. In this case, the data processor 142 may obtain a final PPG signal by assigning a higher weight to the amount of light detected by the left detector and assigning a lower weight to the amount of light detected by the right detector.

The data processor 142 may estimate bio-information of the user based on the photoacoustic signal of the object, the blood vessel image, and the PPG signal, or combinations thereof. In this case, the bio-information may include blood sugar, triglyceride, blood pressure, heart rate, oxygen saturation, stress, antioxidant index, lactic acid, alcohol, cholesterol, and the like, but is not limited thereto. Hereinafter, for convenience of description, blood sugar will be taken as an example of the bio-information.

For example, the data processor 142 may calculate a blood sugar value by inversely tracking the concentration of a light-absorbing material according to the magnitude of the photoacoustic signal.

In another example, the data processor 142 may estimate a change in the diameter of a blood vessel by analyzing a blood vessel image before and after occlusion of the blood vessel. In addition, blood sugar may be estimated based on the change in the diameter of the blood vessel. In this case, the data processor 142 may extract features including information, such as a vascular contraction rate, a vascular dilation rate, a vascular restoration rate, and a vascular diameter change trend of the blood vessel, and may estimate the user's blood sugar based on the extracted features. However, various exemplary embodiments are not limited thereto.

In yet another example, the data processor 142 may correct the obtained photoacoustic signal and the blood sugar value, which is estimated through the blood sugar value, through the obtained PPG signal, or conversely may correct the blood sugar value, which is estimated by extracting features of the PPG signal, through the obtained photoacoustic signal and the blood vessel image.

The data processor 142 may obtain the PPG signal according to the distance between the light incident position on the object and the detector 130. The process in which the data processor 142 obtains a PPG signal according to the distance between the light incident position on the object and the detector 130 will be described with reference to FIG. 2B.

Figure 2B:
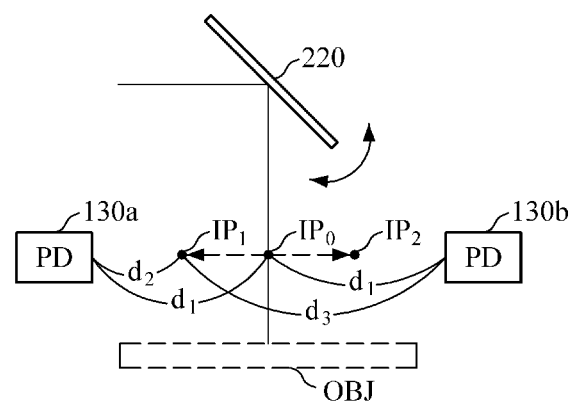
FIG. 2B is a diagram illustrating examples of a distance between an adjusted light incident position on an object and a detector.

FIG. 2B is a diagram illustrating examples of a distance between a light incident position adjusted on an object and a detector 130. Referring to FIG. 2B, the light incident position on the object OBJ may be adjusted between positions IP1 and IP2 according to the adjustment of the angle of the scanner 220 with respect to the center point IP0 between two detectors 130a and 130b.

In this case, the data processor 142 may obtain a PPG signal according to each distance between each of the detectors 130a and 130b and the light incident position IP on the object OBJ.

If the light incident position is located at IP0, the distance between the light incident position IP0 and each of the detectors 130a and 130b is d1. In this case, the data processor 142 may choose one of the PPG signals measured by each of the detectors 130a and 130b, or combine (e.g., average or normalize) the two PPG signals and obtain a PPG signal when the distance between the light incident position and the detector is d1.

When the light incident position is located at IP1, the distance between the light incident position IP1 and the detector 130a is d2, and the distance between the light incident position IP1 and the detector 130b is d3. When the light incident position is located at IP2, the distance between the light incident position IP2 and the detector 130a is d3, and the distance between the light incident position IP2 and the detector 130b is d2.

In this case, the data processor 142 may choose one of the PPG signal measured by the detector 130a when the light incident position is located at IP1 and the PPG signal measured by the detector 130b when the light incident position is located at IP2, or may combine the two PPG signals and obtain a PPG signal when the distance between the light incident position and the detector is d2. Even when the distance between the light incident position and the detector is d3, the data processor 142 may obtain a PPG signal in a similar manner as in the case where the distance between the light incident position and the detector is d2.

The data processor 142 may obtain a final PPG signal by combining the obtained PPG signals for each distance between the light incident position and the detector.

Figure 3:
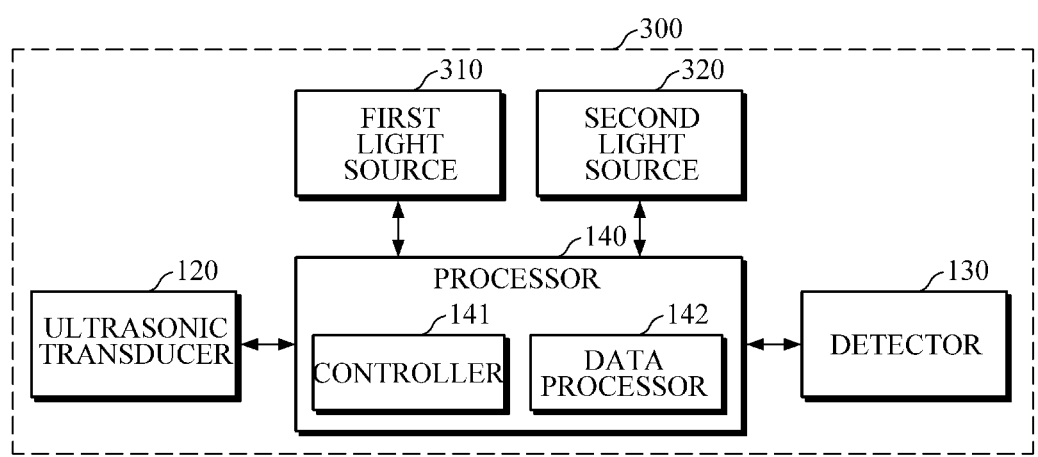
FIG. 3 is a block diagram illustrating an apparatus for measuring a bio-signal according to another exemplary embodiment.

FIG. 3 is a block diagram illustrating an apparatus for measuring a bio-signal according to another exemplary embodiment. Referring to FIG. 3, an apparatus 300 for measuring a bio-signal may include a first light source 310, a second light source 320, an ultrasonic transducer 120, a detector 130, and a processor 140. The ultrasonic transducer 120 and the detector 130 are described in detail with reference to FIG. 1, and thus a duplicate description of components described above will be omitted.

The first light source 310 may emit first light used to measure a photoacoustic signal. In this case, the first light may be a collimated beam, but is not limited thereto. The second light source 320 may emit second light used to measure a PPG signal.

The first light source 310 and/or the second light source may include an LED, an LD, a phosphor, or the like, but are not limited thereto.

The first light source 310 and the second light source 320 may be of the same type or of different types. For example, both of the first light source 310 and the second light source 320 may be LDs, or the first light source 310 may be an LD and the second light source 320 may be an LED.

The wavelength range of light emitted by the first light source 310 and/or the second light source 320 may include various wavelength ranges, such as the IR range, the visible light range, the NIR range, etc. In this case, the wavelength, intensity, driving time of the first light and the second light may be different from each other, but various exemplary embodiments of the present disclosure are not limited thereto.

The processor 140 may include a controller 141 and a data processor 142.

The controller 141 may control the first light source 310 and the second light source 320, and as described above with reference to FIG. 1, may control the operation of the ultrasonic transducer 120, the detector 130, a scanner (not shown), a scanner controller (not shown), and the like.

The controller 141 may control the first light source 310 and the second light source 320 such that the intensity, wavelength, driving method, driving time, and the like of the light emitted by each of the light sources 310 and 320 is different from each other.

For example, the controller 141 may drive the first light source 310 when the scanner rotates in a first direction, for example, counterclockwise direction, and may drive the second light source 320 when the scanner rotates in a second direction, for example, clockwise direction.

In another example, the controller 141 may control the first light source 310 to emit light in a pulse driving manner, and control the second light source 320 to continuously emit light (in a constant wave manner).

In yet another example, the controller 141 may control the first light source 310 to emit a collimated beam and control the second light source 320 to emit light of a plurality of wavelength ranges. However, various embodiments of the present disclosure are not limited thereto.

The data processor 142 may receive the photoacoustic signal measured by the ultrasonic transducer 120 and the PPG signal measured by the detector 130 as described above with reference to FIG. 1.

As described above with reference to FIG. 1, the data processor 142 may obtain a blood vessel image of the object based on the received photoacoustic signal, perform preprocessing on the received PPG signal, and when the detector 130 is provided in plural, may combine the amounts of light detected by each of the detectors 130. Detailed description thereof will be omitted.

When the second light source 320 emits light of a plurality of wavelength ranges, the data processor 142 may obtain a final PPG signal by assigning a wavelength-specific weight to the amount of light of each wavelength detected by the detector 130.

The arrangement of the first light source 310 and the second light source 320 and a difference between optical paths of the first light and the second light according to the arrangement will be described with reference to FIGS. 4 and 5.

Figure 4:
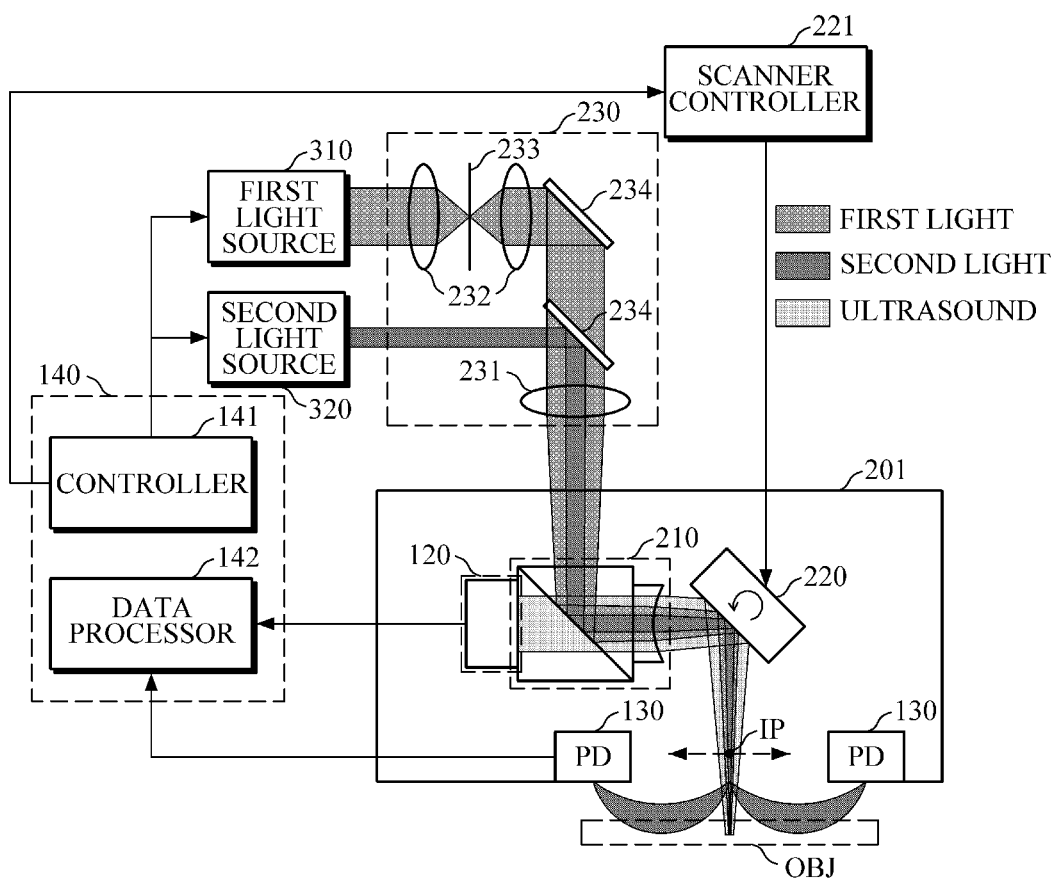
FIG. 4 is a diagram illustrating an example in which a second light source is disposed adjacent to a first light source.

FIG. 4 is a diagram illustrating an example in which the second light source 320 is disposed adjacent to the first light source 310. FIG. 4 illustrates that the second light source 320 is disposed below the first light source 310, but various exemplary embodiments of the present disclosure are not limited thereto. For example, the second light source 320 may be disposed above or next to the first light source 310.

Referring to FIG. 4, the apparatus for measuring a bio-signal according to one exemplary embodiment may include a first light source 310, a second light source 320, an ultrasonic transducer 120, a detector 130, a processor 142, a housing 201, a photoacoustic coupler 210, a scanner 220, a scanner controller 221, and a light transmitter 230. Description of the components described above in FIGS. 1 to 3 will be omitted.

Referring to FIG. 4, first light emitted from the first light source 310 and second light emitted from the second light source 320 may be transmitted by the light transmitter 230 in the direction of the photoacoustic coupler 210 and/or the ultrasonic transducer 120.

In this case, the first light may pass through collimators 232 that makes the emitted light into a parallel light beam, and a pin hole 233 disposed between the collimators 232, as in FIG. 2A, then be reflected by a light reflective mirror 234 and transmitted in the direction of the photoacoustic coupler 210, passing through an objective lens 231 that condenses the parallel light beam to the photoacoustic coupler 210.

The second light may be emitted from the second light source 320 and reflected by the light reflective mirror 234, and then be transmitted in the direction of the photoacoustic coupler 210, passing through the objective lens 231.

Thereafter, the first light and the second light may be reflected by the photoacoustic coupler 210 in the direction of the scanner 220, as in FIG. 2A, and may be reflected by the scanner 220 in the direction of the object.

In this case, the scanner controller 221 including a motor-based device and the like may control the angle of the scanner 220 as described above with reference to FIG. 2A. For example, the scanner controller 221 may control the scanner 220 to vibrate and rotate in a reciprocal manner within a predetermined angle range (e.g., within 20 degrees). The scanner controller 221 may adjust a light incident position IP on the object OBJ by controlling the angle of the scanner 220. The data processor 142 may obtain a PPG signal according to the distance between the light incident position on the object and the detector 130 as described above with reference to FIGS. 1 and 2B. Detailed description thereof will be omitted.

At this time, as described above with reference to FIG. 3, the controller 141 may drive the first light source 310 when the scanner 220 rotates in the first direction, for example, counterclockwise direction, and may drive the second light source 320 when the scanner 220 rotates in the second direction, for example, clockwise direction.

As described above with reference to FIG. 1, there is only a very short time delay between the photoacoustic signal detection by the ultrasonic transducer 120 and the PPG signal measurement by the detector 130, so that the two signals are naturally synchronized with each other.

Figure 5:
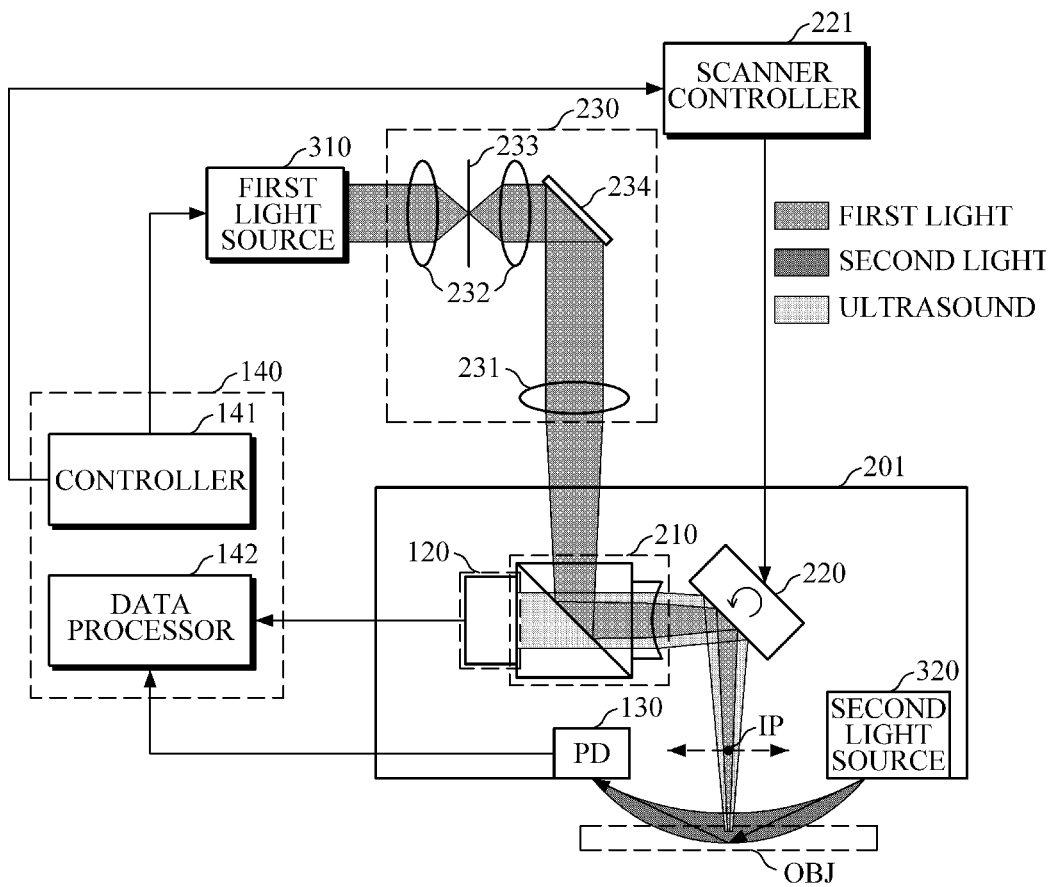
FIG. 5 is a diagram illustrating an example in which the second light source is disposed adjacent to an object.

FIG. 5 is a diagram illustrating an example in which the second light source is disposed adjacent to an object. Hereinafter, the configurations described above with reference to FIGS. 1 to 4 will be omitted.

It is illustrated that there is one detector 130 in FIG. 5, but various exemplary embodiments of the present disclosure are not limited thereto, and the number of detectors 130 may be varied without limitation.

Referring to FIG. 5, the first light emitted from the first light source 310 may be incident into the object OBJ, passing through the light transmitter 230, the photoacoustic coupler 210, and the scanner 220, and the second light source 320 may be disposed adjacent to the object inside the housing 201 and may emit the second light directly to the object OBJ.

At this time, as described above with reference to FIG. 3, the controller 141 may drive the first light source 310 when the scanner 220 rotates in the first direction, for example, counterclockwise direction, and may drive the second light source 320 when the scanner 220 rotates in the second direction, for example, clockwise direction. In this case, there is only a very short time delay between the point in time of photoacoustic signal detection by the ultrasonic transducer 120 and the point in time of PPG signal measurement by the detector 130, so that the two signals are naturally synchronized with each other.

Figure 6:
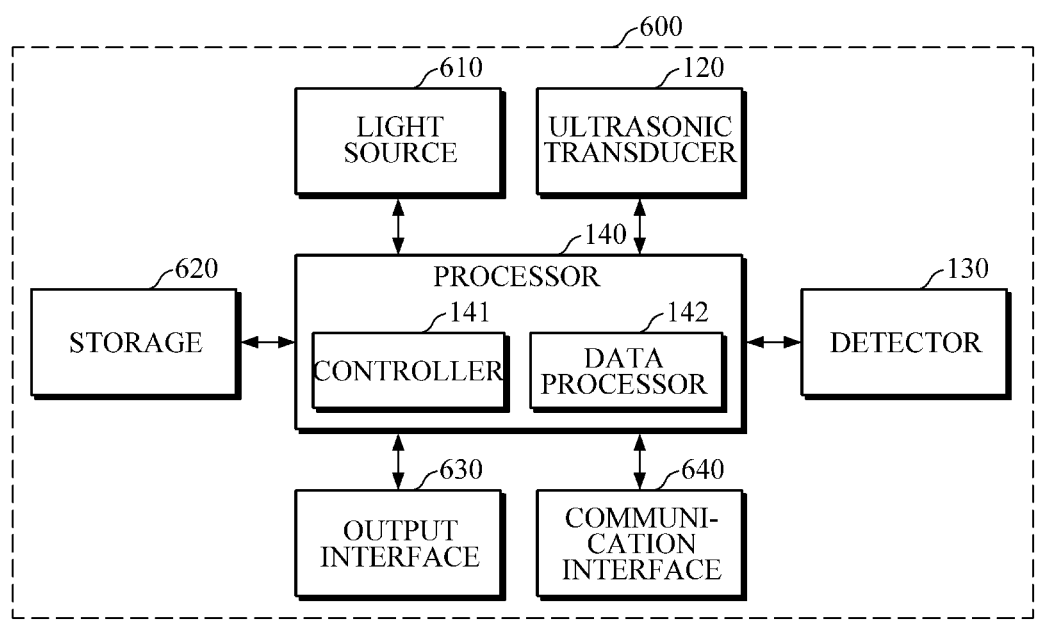
FIG. 6 is a block diagram illustrating an apparatus for measuring a bio-signal according to yet another embodiment.

FIG. 6 is a block diagram illustrating an apparatus for measuring a bio-signal according to yet another embodiment. Referring to FIG. 6, an apparatus 600 for measuring a bio-signal may include a light source 610, a storage 620, an output interface 630, and a communication interface 640 in addition to the ultrasonic transducer 120, the detector 130, and the processor 140 which are described above with reference to FIGS. 1 and 3.

The light source 610 may refer to the light source 110 of FIG. 1, or the first light source 310 and the second light source 420 of FIG. 3.

The storage 620 may store reference information required for measuring bio-information or estimating bio-information, and processing results of the ultrasonic transducer 120, the detector 130, and/or the processor 140. In this case, the reference information may include information on the brightness state of the light source, the concentration range to be estimated for each bio-information, information on the condition or location of the object, user information, such as user's age, gender, health condition, etc., a normal contact state, such as the contact position of the object, light source driving conditions, and the like. However, various exemplary embodiments of the present disclosure are not limited thereto.

In this case, the storage 620 may include at least one storage medium of a flash memory type memory, a hard disk type memory, a multimedia card micro type memory, a card type memory (e.g., an SD memory, an XD memory, etc.), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, and the like, but is not limited thereto.

When a result of measuring a bio-signal and/or an estimated bio-information value are obtained, the output interface 630 may visually display the result of measuring a bio-signal and/or the estimated bio-information value through a display. In this case, when the bio-information estimation result falls outside a normal range, alarm/warning information may be visually output. Alternatively, warning information on the contact state, contact force, and estimated bio-information value may be output using a non-visual output means, such as a voice or haptic device.

The communication interface 640 may communicate with an external device under the control of the processor 140 to transmit and receive various data related to bio-signal measurement and/or bio-information estimation.

For example, the communication interface 640 may transmit the processing result of the processor 120 to an external device, and allow the external device to manage the bio-information history for the user, monitor the user's health condition, output the bio-information history and the monitoring result of the health condition, and the like. In this case, the external device includes a smartphone, a tablet PC, a desktop PC, a notebook PC, a TV, a home monitor, a panel monitor of a refrigerator, and the like, and may include a device used in a medical institution including an invasive blood sugar measurement device and a body composition measurement device, but is not limited thereto.

In another example, the communication interface 640 may receive a light source driving method, characteristic information, such as a blood vessel image of a user, and the like from the external device. The received information may be stored in the storage 620.

In this case, the communication interface 640 may communicate with the external device by using Bluetooth communication, Bluetooth low energy (BLE) communication, near field communication (NFC), wireless local access network (WLAN) communication, ZigBee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, and/or 5G communication. However, these are merely examples, and the exemplary embodiments of the present disclosure are not limited thereto.

Figure 7:
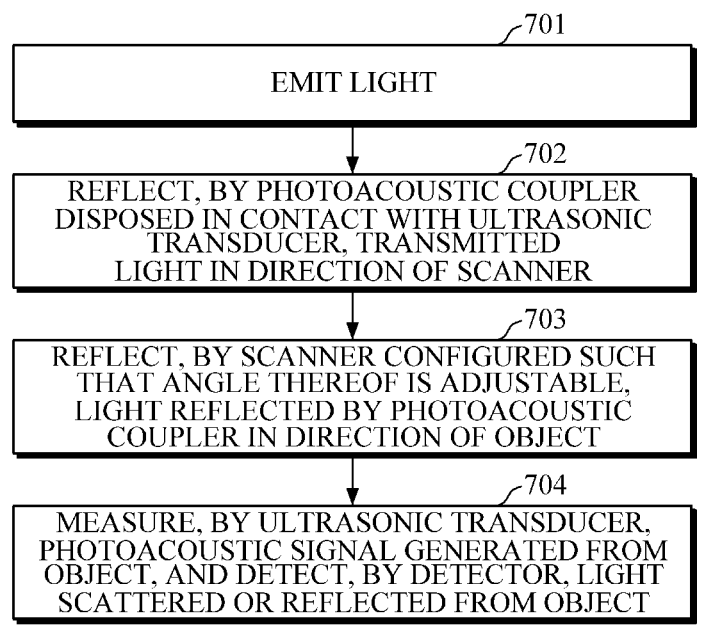
FIG. 7 is a flowchart illustrating a method of measuring a bio-signal according to an exemplary embodiment.

FIG. 7 is a flowchart illustrating a method of measuring a bio-signal according to an exemplary embodiment. The method of FIG. 7 may be one exemplary embodiment of a method performed by the apparatuses 100, 300, and 600 according to the exemplary embodiments of FIGS. 1, 3, and 6. The method is described in detail above and thus will be set forth in brief to avoid redundancy.

First, light may be emitted in operation 701. In this case, a single light source may emit the light, or a plurality of light sources may emit light of different intensities and different wavelengths.

Then, a photoacoustic coupler disposed in contact with an ultrasonic transducer may reflect the transmitted light in the direction of a scanner in operation 702. In this case, the photoacoustic coupler may be made of aluminum or gold material to reflect the light and pass the photoacoustic signal, but is not limited thereto.

Then, in operation 703, the scanner configured such that an angle thereof can be adjusted may reflect the light, which has been reflected by the photoacoustic coupler, in the direction of an object. In this case, the angle of the scanner may be adjusted by a scanner controller that includes a conventional motor-based device.

Then, in operation 704, an ultrasonic transducer may measure a photoacoustic signal generated from the object, and a detector may detect light scattered or reflected from the object. In this case, a blood vessel image of the object may be obtained based on the measured photoacoustic signal, and a PPG signal may be obtained based on the light detection result of the detector. Detailed description thereof will be omitted.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for measuring a bio-signal, the apparatus comprising:
   a light source configured to emit light;
   an ultrasonic transducer configured to obtain a photoacoustic signal generated from an object;
   a photoacoustic coupler disposed in contact with the ultrasonic transducer and configured to direct the light transmitted from the light source to a scanner and to direct the photoacoustic signal generated from the object to the ultrasonic transducer;
   the scanner configured to reflect the light incident from the photoacoustic coupler to the object, and reflect the photoacoustic signal generated from the object to the photoacoustic coupler;
   a scanner controller configured to adjust a light incident position on the object by controlling an angle of the scanner;
   a plurality of light detectors configured to obtain a light signal by assigning a weight based on a distance between the light incident position on the object and each of the plurality of detectors, and computing a weighted sum of an amount of light detected by each of the plurality of light detectors, based on the light incident position being placed between the plurality of light detectors; and
   a processor configured to obtain bio-information based on the light signal and the photoacoustic signal,
   wherein the scanner controller is further configured to adjust the light incident position to be placed between the plurality of light detectors by adjusting the angle of the scanner while the light source, the ultrasonic transducer, and the plurality of light detectors are placed at fixed positions, and allow a first distance between one of the plurality of light detectors and the light incident position to increase as a second distance between another one of the plurality of light detectors and the light incident position decreases, and
   wherein the processor is configured to obtain a blood vessel image of the object based on the photoacoustic signal for each light incident position.

2. The apparatus of claim 1, wherein the scanner controller is configured to adjust the light incident position on the object by controlling a tilt angle of the scanner.

3. The apparatus of claim 2, wherein the processor is configured to obtain the blood vessel image of the object based on the photoacoustic signal for each light incident position, and obtain a photoplethysmography (PPG) signal according to a distance between the adjusted light incident position and one of the plurality of light detectors.

4. The apparatus of claim 1, further comprising a light transmitter configured to transmit the light emitted from the light source to the photoacoustic coupler.

5. The apparatus of claim 4, wherein the light transmitter comprises an objective lens for condensing the light emitted from the light source to the photoacoustic coupler.

6. The apparatus of claim 1, wherein the processor is configured to pulse drive the light source, or to continuously drive the light source by modulating a light intensity according to time.

7. An apparatus for measuring a bio-signal, the apparatus comprising:
   a first light source configured to emit a first light;
   an ultrasonic transducer configured to obtain a photoacoustic signal generated from an object;
   a photoacoustic coupler disposed in contact with the ultrasonic transducer and configured to reflect the first light transmitted from the first light source to a scanner and to direct the photoacoustic signal generated from the object to the ultrasonic transducer;
   the scanner configured to reflect the light incident from the photoacoustic coupler to the object, and reflect the photoacoustic signal generated from the object to the photoacoustic coupler;
   a second light source configured to emit a second light to measure a photoplethysmography (PPG) signal;
   a plurality of light detectors configured to measure a light signal by assigning a weight based on a distance between a light incident position on the object and each of the plurality of detectors, and computing a weighted sum of an amount of light detected by each of the plurality of light detectors, based on the light incident position being placed between the plurality of light detectors;
   a processor configured to obtain bio-information based on the light signal and the photoacoustic signal; and
   a scanner controller configured to adjust the light incident position to be placed between the plurality of light detectors by adjusting the angle of the scanner while the light source, the ultrasonic transducer, and the plurality of light detectors are placed at fixed positions, and allow a first distance between one of the plurality of light detectors and the light incident position to increase as a second distance between another one of the plurality of light detectors and the light incident position decreases.

8. The apparatus of claim 7, wherein the scanner controller is further configured to adjust the light incident position by controlling a tilt angle of the scanner.

9. The apparatus of claim 7, further comprising a light transmitter configured to transmit the first light and the second light to the photoacoustic coupler.

10. The apparatus of claim 9, wherein the light transmitter comprises an objective lens for condensing the first light and the second light to the photoacoustic coupler.

11. The apparatus of claim 9, wherein the processor is further configured to obtain a blood vessel image of the object based on the photoacoustic signal for each light incident position, and to obtain the PPG signal according to a distance between the light incident position and one of the plurality of light detectors.

12. The apparatus of claim 7, wherein the first light is reflected by the photoacoustic coupler and the scanner to be incident to the object and the second light source is configured to emit the second light directly to the object.

13. The apparatus of claim 7, wherein the processor is further configured to control the second light source to emit the second light of a plurality of wavelength ranges, and to assign a wavelength-specific weight to the amount of light of each wavelength detected by each of the light detectors.

14. The apparatus of claim 7, wherein at least one of a wavelength and an intensity of the first light and the second light is different from each other.

15. The apparatus of claim 7, wherein the processor is further configured to drive the first light source when the scanner rotates in a first direction, and to drive the second light source when the scanner rotates in a second direction.

16. A method of measuring a bio-signal, the method comprising:
   emitting light;
   directing the light to a scanner, by a photoacoustic coupler disposed in contact with an ultrasonic transducer;
   directing the light incident from the photoacoustic coupler to an object, by the scanner having an adjustable tilt angle;
   obtaining, by the ultrasonic transducer, a photoacoustic signal generated from the object and then is received through the scanner and the photoacoustic coupler; and
   measuring, by a plurality of light detectors, a light signal by assigning a weight based on a distance between a light incident position on the object and each of the plurality of detectors, and computing a weighted sum of an amount of light detected by each of the plurality of light detectors,
   wherein the light incident position is placed between the plurality of light detectors, and
   wherein the directing of the light incident from the photoacoustic coupler comprises: adjusting the light incident position to be placed between the plurality of light detectors by adjusting the angle of the scanner while the light source, the ultrasonic transducer, and the plurality of light detectors are placed at fixed positions, and allowing a first distance between one of the plurality of light detectors and the light incident position to increase as a second distance between another one of the plurality of light detectors and the light incident position decreases.

* * * * *